United States Patent
Yamada et al.

(10) Patent No.: US 6,248,768 B1
(45) Date of Patent: *Jun. 19, 2001

(54) BENZIMIDAZOLE DERIVATIVES AND PHARMACOLOGICALLY ACCEPTABLE SALTS THEREOF

(75) Inventors: Shozo Yamada; Toshiyuki Hosoya; Kazuhiro Kitagawa; Shin-ichi Inoue; Mamoru Kiniwa; Tetsuji Asao, all of Saitama (JP)

(73) Assignee: Taiho Pharmaceutical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 69 days.

(21) Appl. No.: 09/341,277
(22) PCT Filed: Nov. 6, 1998
(86) PCT No.: PCT/JP98/05011
   § 371 Date: Jul. 7, 1999
   § 102(e) Date: Jul. 7, 1999
(87) PCT Pub. No.: WO99/24425
   PCT Pub. Date: May 20, 1999

(30) Foreign Application Priority Data

Nov. 7, 1997 (JP) .................................................. 9-305720

(51) Int. Cl.⁷ ................ A61K 31/4184; A61K 31/4196; A61P 37/00; C07D 235/18; C07D 403/04
(52) U.S. Cl. ........................ 514/383; 514/394; 514/397; 548/255; 548/266.4; 548/304.7; 548/306.1
(58) Field of Search ...................................... 514/359, 383, 514/394, 397; 548/255, 266.4, 304.7, 306.1

(56) References Cited

FOREIGN PATENT DOCUMENTS

| 8-501318 | 2/1996 | (JP) | ................................ C07C/65/26 |
| 8-109169 | 4/1996 | (JP) | ............................. C07D/235/18 |
| 8-134073 | 5/1996 | (JP) | ............................. C07D/513/04 |

*Primary Examiner*—Jane Oswecki
(74) *Attorney, Agent, or Firm*—Sughrue, Mion, Zinn, Macpeak & Seas, PLLC

(57) ABSTRACT

This invention provides a compound having both IL-4 production inhibitory activity and PDE (IV) inhibitory activity, represented by formula (I):

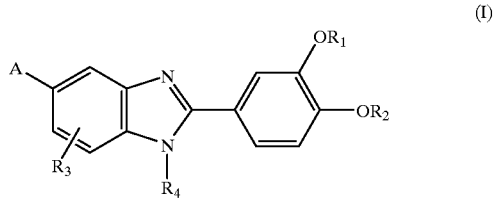

and a pharmaceutical composition or a therapeutic agent for acute and chronic inflammatory diseases and an anti-allergic or anti-inflammatory agent, each of which comprising an effective amount of the compound and a pharmacological carrier. It also provides use of the compound of formula (I) for the production of the aforementioned pharmaceutical composition or therapeutic agent for acute and chronic inflammatory diseases and anti-allergic or anti-inflammatory agent, and a method for treating acute and chronic inflammatory diseases.

25 Claims, 1 Drawing Sheet

BENZIMIDAZOLE DERIVATIVES AND PHARMACOLOGICALLY ACCEPTABLE SALTS THEREOF

This application is a 371 of PCT/JP98/05011 filed Nov. 6, 1998.

TECHNICAL FIELD

This invention relates to benzimidazole derivatives and pharmacologically acceptable salts thereof, which have both of an interleukin (IL)-4 production inhibitory activity and a phosphodiesterase IV (PDE (IV)) inhibitory activity and are useful as therapeutic or preventive drugs for acute and chronic inflammatory diseases such as atopic dermatitis, allergic rhinitis, bronchial asthma and glomerulonephritis. It also relates to a pharmaceutical composition in which the compound of this invention is used.

BACKGROUND ART

Regarding inflammatory diseases, various medicaments capable of inhibiting acute stage inflammations have been developed in recent years, but medicaments which can effectively inhibit chronic stage inflammations are still scarce so that their development is a pressing problem. Also, an anti-inflammatory drug which can be used without distinctions between acute stage and chronic stage is useful in the clinical field.

Under such circumstances, attempts are being made on the research and development of medicaments having phosphodiesterase IV (PDE (IV)) inhibitory activity. This is based on the information that PDE (IV) is concerned in acute and chronic inflammatory diseases (see for example, J. Pharmacol. Exp. Ther., 266(1), 306–313 (1993), Br. J. Pharmacol. , 120(2), 289–297 (1997) and Am. J. Respir. Crit. Care Med., 149(5), 1153–1159 (1994)). In reality, however, drugs so far developed merely having such an activity are effective for acute inflammatory diseases but cannot exert sufficient effects on chronic inflammatory diseases. It is considered that certain members of cytokine produced by Th2 cells as one of the subgroups of CD4$^+$ T cells are taking an important role in the onset of inflammatory diseases, and interleukin (IL)-4 among them is particularly concerned in chronic stage inflammatory diseases (see for example, Am. J. Physiol., 272 (2 Pt 1), L 253–261 (1997), Am. J. Respir. Cell Mol. Biol. , 10(5), 526–532 (1994) and ibid., 13(1), 54–59 (1995)).

In consequence, development of a drug having both PDE (IV) inhibitory activity and IL-4 production inhibitory activity will result in an anti-inflammatory drug which is effective on both acute and chronic inflammatory diseases. At present, PDA-641 has been reported as such a compound (cf. Allergy Clin. Immunol., 93, 286 (1994)), but this compound is not satisfactory because of its weak IL-4 production inhibitory activity.

Benzimidazole derivatives have been broadly studies as medicaments. JP-A-3-14579 describes a benzimidazole derivative having an imidazole group and a triazole group, but the compound is disclosed only as a therapeutic agent for heart diseases and a therapeutic agent for duodenal ulcer, so that the compound has not been known as an anti-inflammatory agent (the term "JP-A" as used herein means an "unexamined published Japanese patent application"). International Publication No. WO 94/12461 describes a benzimidazole derivative which has PDE (IV) inhibitory activity and is used in various inflammatory diseases, but the benzimidazole derivative is different from the compound of the present invention in terms of the presence or absence of triazole ring on the condensed phenyl ring, and its effects on both acute and chronic inflammatory diseases are not as expected.

The present invention contemplates providing a compound which has both IL-4 production inhibitory activity and PDE (IV) inhibitory activity and is useful in treating or preventing acute and chronic inflammatory diseases.

DISCLOSURE OF THE INVENTION

As a result of the extensive investigation, the inventors of the present invention have found that the aforementioned object can be achieved by a novel benzimidazole derivative in which a triazole group is introduced into the 5-position of the benzinidazole nucleus, and substituting positions of two alkoxy groups to be substituted on the phenyl group bonded to the 2-position are specified, thereby resulting in the accomplishment of this invention.

Accordingly, the present invention relates to a benzimidazole derivative represented by formula (I):

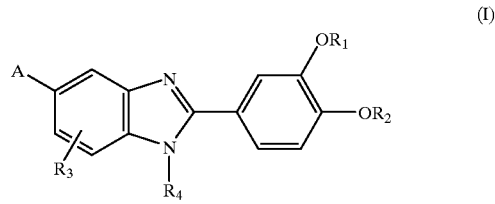

[wherein A represents a triazole group; $R_1$ and $R_2$ may be the same or different from each other and each represents an aliphatic hydrocarbon radical which may have an alicyclic or aromatic hydrocarbon radical or an alicyclic hydrocarbon radical; $R_3$ represents a hydrogen atom or a substituent group; and $R_4$ represents a hydrogen atom or a protective group of the nitrogen atom] or a pharmacologically acceptable salt thereof.

The benzimidazole derivative represented by the just described formula (I) or a pharmacologically acceptable salt thereof (hereinafter, referred to as "compound of the present invention") has excellent actions of both IL-4 production inhibitory activity and PDE (IV) inhibitory activity and is useful for the treatment of various acute and chronic inflammatory diseases.

Thus, the present invention provides a pharmaceutical composition which comprises an effective amount of the compound of the present invention and a pharmacological carrier.

It particularly provides an anti-allergic or anti-inflammatory agent which comprises an effective amount of the compound of the present invention and a pharmacological carrier.

The present invention also provides use of the compound of the present invention for the production of the aforementioned pharmaceutical composition, therapeutic or preventive agent for acute and chronic inflammatory diseases and anti-allergic or anti-inflammatory agent.

The present invention further provides a method for treating and/or preventing acute and chronic inflammatory diseases, which comprises the step of administering an effective amount of the aforementioned compound of the present invention to patients.

According to the present invention, examples of the triazole group of A include 1,2,4-triazol-1-yl, 1,2,4-triazol-4-yl, 1,2,3-triazol-1-yl and 1,2,3-triazol-2-yl, of which 1,2, 4-triazol-1-yl and 1,2,4-triazol-4-yl are preferred and 1,2,4-triazol-1-yl is more preferred.

Examples of the aliphatic hydrocarbon radical in $R_1$ or $R_2$ include straight- or branched-chain lower alkyl groups having 1 to 6 carbon atoms, such as methyl, ethyl, n-propyl, isopropyl, n-butyl, isobutyl, sec-butyl, tert-butyl, n-pentyl, isopentyl and n-hexyl; and straight- or branched-chain lower alkenyl groups having 2 to 6 carbon atoms, such as vinyl, 1-propenyl, allyl, dimethylallyl, isopropenyl, 1-butenyl, 2-butenyl, 1-methyl-2-butenyl, 1,3-butanedienyl, 1-pentenyl, 2-pentenyl, 2-hexenyl and 1,4-hexanedienyl; of which straight- or branched-chain lower alkyl groups having 1 to 6 carbon atoms are preferred, and methyl, isopropyl and isopentyl are particularly preferred.

Examples of the aliphatic hydrocarbon radical having an alicyclic hydrocarbon radical according to $R_1$ or $R_2$ include the aforementioned aliphatic hydrocarbon radicals further having monocyclic alicyclic hydrocarbon radicals having 3 to 7 carbon atoms, which may have a straight- or branched-chain saturated lower alkyl group having 1 to 3 carbon atoms, such as cyclopropyl, cyclobutyl, cyclopentyl, cyclopentenyl, cyclohexyl, 3-isopropyl-cyclohexyl, cyclohexenyl, 2-methyl-2-cyclohexenyl, 3-methyl-2-cyclohexenyl, 4-ethyl-2-cyclohexenyl, cycloheptanyl and cycloheptenyl; or having alicyclic hydrocarbon radicals of cross-linked ring or polycyclic system, such as bicyclobutanyl, bicyclooctanyl, norbornyl, norborenyl and indanyl; and preferred are straight- or branched lower alkyl groups having 1 to 6 carbon atoms substituted with a monocyclic alicyclic hydrocarbon radical having 3 to 7 carbon atoms, more preferably cyclopropylmethyl and cyclopentylmethyl.

Examples of the aliphatic hydrocarbon radical having an aromatic hydrocarbon radical according to $R_1$ or $R_2$ include the aforementioned aliphatic hydrocarbon radicals further having an aromatic hydrocarbon radical such as phenyl or naphthyl, of which an aliphatic hydrocarbon radical having phenyl group is preferred, and benzyl, phenylethyl, phenylpropyl and cinnamyl are particularly preferred.

Examples of the alicyclic hydrocarbon radical according to $R_1$ or $R_2$ include the aforementioned monocyclic alicyclic hydrocarbon radicals having 3 to 7 carbon atoms, which may have a straight- or branched-chain saturated lower alkyl group having 1 to 3 carbon atoms, and the aforementioned alicyclic hydrocarbon radicals of cross-linked ring or polycyclic system, of which monocyclic alicyclic hydrocarbon radicals having 3 to 7 carbon atoms are preferred, and cyclopentyl, cyclopentenyl, cyclohexenyl and cycloheptenyl are particularly preferred.

Among compounds of the present invention, certain compounds having asymmetric carbons exist in optical isomer forms and geometrical isomer forms depending on the number of asymmetric carbons, and all of these isomers are included in the present invention.

Though conventionally used optical resolution methods can be used for the isolation of optically active substances of the compound of the present invention, the optically active substances can also be obtained by fractionating them by HPLC using an optically active column. An example of the optically active column is CHIRALPAK AD manufactured by Daicel Chemical Industries.

$R_3$ is a hydrogen atom or a substituent group, and examples of the substituent group include a lower alkoxy group, a lower alkyl group, a hydroxyl group, a nitro group, a cyano group, an amino group and a halogen atom, but $R_3$ is preferably a hydrogen atom or a lower alkoxy group. Examples of the lower alkoxy group include straight- or branched-chain alkoxy groups having 1 to 6 carbon atoms, such as imethoxy, ethoxy, n-propoxy, isopropoxy, n-butoxy, isobutoxy, sec-butoxy, tert-butoxy, n-pentyloxy, cyclopentyloxy, isopentyloxy, n-hexyloxy and cyclohexyloxy, of which methoxy, ethoxy and pentyloxy are preferred, and methoxy and n-pentyloxy are more preferred. Examples of the lower alkyl group include straight- or branched-chain alkyl groups having 1 to 6 carbon atoms, such as methyl, ethyl, n-propyl, isopropyl, n-butyl, isobutyl, sec-butyl, t-butyl, n-pentyl, isopentyl and n-hexyl, of which methyl and ethyl are preferred. Examples of the halogen atom include fluorine, chlorine, bromine and iodine.

The substituent group of $R_3$ can be substituted at least at one of the 4-, 6- and 7-positions of the benzimidazole nucleus, but preferably at the 6-position.

The nitrogen atom-protective group of P may be any group which can be hydrolyzed easily in the living body, and its examples include acyl groups such as acetyl, benzoyl and pivaloyl; alkoxycarbonyl groups such as methoxycarbonyl, ethoxycarbonyl and benzyloxycarbonyl; aryloxycarbonyl groups such as phenoxycarbonyl; straight- or branched-chain lower alkyl groups having 1 to 6 carbon atoms, such as methyl, ethyl, n-propyl, isopropyl, n-butyl, isobutyl, sec-butyl, tert-butyl, n-pentyl, isopentyl and n-hexyl; hydroxy lower alkyl groups such as hydroxymethyl and hydroxyethyl; aralkyl groups such as benzyl and trityl; alkoxyalkyl groups such as methoxymethyl, ethoxymethyl, methoxyethyl and ethoxyethyl; alkoxyalkoxyalkyl groups such as methoxymethoxymethyl, methoxyethoxymethyl, ethoxyethoxymethyl and ethoxyethoxyethyl; and aralkyloxyalkyl groups such as benzyloxymethyl, trityloxymethyl, benzyloxyethyl and trityloxyethyl.

Examples of the pharmacologically acceptable salt of the benzimidazole derivative of the present invention represented by the formula (I) include mineral acid salts such as hydrochloride, sulfate and nitrate, and organic acid salts such as fumarate, maleate, tartarate, toluenesulfonate and methanesulfonate.

The compound of the present invention may exist in tautomer forms based on the benzimidazole skeleton, and such isomers are also included in the present invention.

Also, the compound of the present invention may be in the form of solvates including hydrates, and amorphous or polymorphic forms.

Regarding the aforementioned formula (I), preferred is a benzimidazole derivative or a pharmacologically acceptable salt thereof, in which A is 1,2,4-triazol-1-yl or 1,2,4-triazol-4-yl, $R_1$ and $R_2$ may be the same or different from each other and each is a straight- or branched lower alkyl group having 1 to 6 carbon atoms, which may have a monocyclic alicyclic hydrocarbon radical having 3 to 7 carbon atoms, or a monocyclic alicyclic hydrocarbon radical having 3 to 7 carbon atoms, $R_3$ is a hydrogen atom or a lower alkoxy group and $R_4$ is a hydrogen atom, and more preferred is a benzimidazole derivative or a pharmacologically acceptable salt thereof, in which A is 1,2,4-triazol-1-yl, $R_1$ and $R_2$ may be the same or different from each other and each is methyl, isopropyl, isopentyl, cyclopropylmethyl, cyclopentylmethyl, cyclopentyl, cyclopentenyl, cyclohexenyl or cycloheptenyl, $R_3$ is a hydrogen atom and $R_4$ is a hydrogen atom.

The benzimidazole derivative of the present invention represented by the formula (I) can be produced using various compounds as the materials. For example, the benzimidazole derivative is produced by a method shown by the following reaction process A, in accordance with the methods described in "Heterocyclic Compounds Benzimidazoles and Congeric Tricyclic Compounds, Part 1,2" edited by P. N. Preston and "Comprehensive Heterocyclic Chemistry, Vol.5" edited by A. R. Katritzky and C. W. Rees.

(Reaction process A)

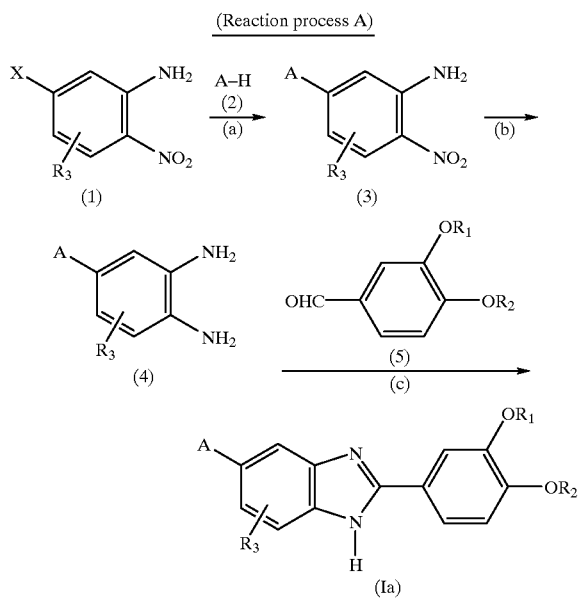

In the above formulae, A, $R_1$, $R_2$ and $R_3$ are as defined in the foregoing, and X is a halogen atom.

Illustratively, each step of the above reaction process A is carried out in the following manner.

(Step a)

The compound represented by the formula (3) can be produced by allowing the known compound (1) as disclosed, for example, in *Journal of Chemical Society*, Perkin Trans I, 2751 (1994) to react with the known compound (2) in N,N-dimethylformamide in the present of a base, in accordance with the methods as disclosed, for example, in *Journal of Medicinal Chemistry*, Vol. 35, No. 23, 4455–4463 (1992) and JP-A-3-14579.

Examples of the base include potassium carbonate, sodium carbonate and sodium hydride. In carrying out the reaction, 1 to 2 moles of the compound (2) and base are used based on 1 mole of the compound (1). The reaction temperature is generally from about 50 to 150° C., preferably from 100 to 120° C. The reaction time is generally from 0.5 to 24 hours, preferably from 3 to 6 hours.

(Step b)

The compound represented by the formula (4) is produced by reducing the compound represented by the formula (3). The reduction method may be selected from the following methods 1) to 3).

1) The compound is reduced by hydrogenation in an inert solvent in the presence of a catalyst. The inert solvent is not particularly limited, with the proviso that it does not take part in the reaction, and its examples include methanol, ethanol and ethyl acetate. Examples of the catalyst include palladium-carbon, Raney nickel and platinum oxide. The catalyst is used in an amount of from 0.1 to 0.5 g, based on 1 g of the compound of formula (3). The reaction is carried out under a hydrogen pressure of from 1 to 20 kg/cm$^2$ at a reaction temperature of from roam temperature to 60° C. for a period of from 1 to 4 hours.

2) The compound is reduced in an acidic or alkaline solvent in the presence of a metal or metal salt. Examples of the metal and metal salt include zinc, aluminum, tin, iron, stannous chloride, ferrous chloride and ferrous sulfate. Examples of the acidic solvent include acetic acid, hydrochloric acid and sulfuric acid, each alone or as a combination with water, methanol or ethanol. Examples of the alkaline solvent include liquid ammonia, sodium hydroxide aqueous solution and potassium hydroxide aqueous solution. The metal or metal salt is used in an amount of from 3 to 50 moles, preferably from 5 to 10 moles, based on the compound (3). The temperature of this reaction is generally from 50 to 150° C., preferably from 80 to 120° C. The reaction is carried out for a period of from 0.5 to 24 hours, preferably from 2 to 6 hours.

3) The compound is reduced by hydrazine in an appropriate solvent in the presence of a metal salt or metal oxide and activated carbon. Examples of the metal salt and metal oxide include ferric chloride and ferric oxide. The solvent is not particularly limited, with the proviso that it does not take part in the reaction, and its examples include methanol, ethanol and ethyl acetate. The metal salt or metal oxide is used in an amount of from 0.6 to 1.0 mole %, activated carbon is used in an amount of $\frac{1}{10}$ by weight and hydrazine is used in an amount of from 1.5 to 2.0 moles, based on the compound (2). The temperature of this reaction is generally from 50 to 100° C., preferably reflux temperature of the solvent used. The reaction is carried out for a period of from 0.5 to 24 hours, preferably from 2 to 6 hours.

(Step c)

The benzimidazole derivative of formula (Ia) is produced by allowing the compound of formula (4) to react with the benzaldehyde derivative of formula (5) in an appropriate solvent in the presence of an oxidizing agent or sodium hydrogen sulfite.

The solvent is not particularly limited, with the proviso that it does not take part in the reaction, and its examples include methanol, ethanol, dimethylformamide, dimethylacetamide and nitrobenzene. The benzaldehyde derivative (5) is used in an amount of from 1.0 to 1.5 moles, the oxidizing agent is used in an amount of from 1.0 to 2.0 moles and sodium hydrogen sulfite, if used, is used in the same amount, based on the compound (4). The reaction temperature is from 70 to 150° C., and the reaction time is from 1 to 18 hours.

The benzaldehyde derivative of formula (5) can be produced in accordance with the method described in *Journal of Medicinal Chemistry*, Vol. 37, pp. 1696–1703 (1994), using vanillin or isovanillin as the material and carrying out its alkylation with corresponding alkyl halide in N,N-dimethylformamide in the presence of a base. Examples of the base include potassium carbonate, sodium carbonate, sodium hydroxide, potassium hydroxide and sodium hydride. In carrying out the reaction, 1 to 2 moles of an alkyl halide and 1 to 2 moles of a base are used based on 1 mole of the starting material. The temperature of this reaction is generally from 50 to 150° C., preferably from 60 to 90° C. The reaction time is generally from 0.5 to 24 hours, preferably from 4 to 8 hours.

The derivative can also be produced by carrying out alkylation of a corresponding alcohol compound with triphenylphosphine and diethyl azodicarboxylate in tetrahydrofuran under dehydration. In carrying out the reaction, 1 to 2 moles of the alcohol compound, triphenylphosphine and diethyl azodicarboxylate are used based on 1 mole of the starting material. The reaction temperature is from room temperature to reflux temperature of the solvent, and the reaction time is from 1 to 24 hours.

The compound (Ia) of the present invention thus obtained by the aforementioned reaction process A may has a protective group introduced to the nitrogen atom on the benzimidazole skeleton in accordance with ordinary methods as disclosed, for example, in International Publication No. WO93/14083.

The compound of the present invention thus obtained by the aforementioned reaction process A can be easily isolated and purified from the reaction mixture by usually used separation and purification means such as column chromatography, recrystallization and evaporation under reduced pressure.

The pharmaceutical composition, therapeutic or preventive agent for acute and chronic inflammatory diseases and anti-allergic or anti-inflammatory agent of the present invention can be made into pharmaceutical preparation compositions in the usual way using appropriate pharmaceutical carriers. Examples of the carriers to be used include those which are generally used in drugs, such as a filler, a binder, a disintegrating agent, a lubricant, a coloring agent, a flavor corrective, an order corrective and a surface active agent.

Dosage form of the pharmaceutical composition of the present invention when used as a therapeutic agent in mammals including human is not particularly limited and can be selected optionally depending on each therapeutic purpose, and its illustrative examples include parenteral preparations such as injections, suppositories, external preparations (e.g., ointments and adhesives) and aerosols, and oral preparations such as tablets, coated tablets, powders, granules, capsules, solutions, pills, suspensions and emulsions.

The aforementioned various drugs are made into pharmaceutical preparations by ordinary preparation methods known in the field.

In forming oral solid dosage forms such as tablets, powders and granules, examples of the carriers to be used include fillers such as lactose, sucrose, sodium chloride, glucose, urea, starch, calcium carbonate, kaolin, crystalline cellulose, silicic acid, methyl cellulose, glycerol, sodium alginate and acacia, binders such as simple syrup, glucose solution, starch solution, gelatin solution, polyvinyl alcohol, polyvinyl ether, polyvinyl pyrrolidone, carboxymethyl cellulose, shellac, methyl cellulose, ethyl cellulose, hydroxypropyl cellulose, water, ethanol and potassium phosphate, disintegrating agents such as dry starch, sodium alginate, agar powder, laminaran powder, sodium bicarbonate, calcium carbonate, polyoxyethylene sorbitan fatty acid esters, sodium lauryl sulfate, stearic acid monoglyceride, starch and lactose, disintegration inhibitors such as sucrose, stearic acid, cacao butter and hydrogenated oil, absorption accelerating agents such as quaternary ammonium base and sodium lauryl sulfate, moisture keeping agents such as glycerol and starch, adsorbents such as starch, lactose, kaolin, bentonite and colloidal silica and lubricants such as purified talc, stearic acid salt, boric acid powder and polyethylene glycol. As occasion demands, tablets can be made into coated tablets using usual coatings, such as sugar coated tablets, gelatin coated tablets, enteric coated tablets, film coated tablets, double-layer tablets and multi-layer tablets. In forming the dosage form of pills, examples of the carriers to be used include fillers such as glucose, lactose, starch, cacao butter, hardened plant oil, kaolin and talc, binders such as powdered acacia, powdered tragacanth, gelatin and ethanol, and disintegrating agents such as laminaran and agar.

Capsules are prepared by mixing the active ingredient with the aforementioned various carriers and filling appropriate capsules such as hard gelatin capsules or soft capsules with the mixture.

The dosage form of suppositories can be formed by adding an appropriate absorption accelerating agent to carriers such as polyethylene glycol, cacao butter, lanolin, higher alcohol, higher alcohol esters, gelatin, semi-synthetic glyceride and Witepsol (trade name, manufactured by Dynamite Novel).

Examples of the carriers to be used in forming the dosage form of injections include diluents such as water, ethyl alcohol, macrogol, propylene glycol, ethoxylated isostearyl alcohol, polyoxylated isostearyl alcohol and polyoxyethylene sorbitan fatty acid esters, pH adjusting agents and buffers such as sodium citrate, sodium acetate and sodium phosphate, and stabilizing agents such as sodium pyrosulfite, ethylenediaminetetraacetic acid, thioglycollic acid and thiolactic acid. In this case, the pharmaceutical preparation may contain sodium chloride, glucose or glycerol in an amount sufficient enough for preparing isotonic solution. It may also contain other additives such as a solubilization assisting agent, a soothing agent and a local anesthetic. By adding these carriers, subcutaneous, intramuscular and intravenous injections can be produced in the usual way.

The liquid preparations may be aqueous or oily suspensions, solutions, syrups or elixirs, and they are prepared using general additive agents in the usual way.

When the dosage form of ointments such as pastes, creams and gels are prepared, generally used materials such as a base, a stabilizing agent, a moistening agent and a preservative are formulated and mixed in response to each purpose and made into respective preparations. Examples of the base to be used include white petrolatum, paraffin, glycerol, a cellulose derivative, polyethylene glycol, silicon and bentonite. Examples of the preservative to be used include methyl parahydroxybenzoate, ethyl parahydroxybenzoate and propyl parahydroxybenzoate.

Adhesive preparations can be produced in the usual way by coating the aforementioned ointments such as creams, gels or pastes on a conventional support. Examples of the suitable support include woven or non-woven fabrics made of cotton, rayon or chemical fiber and films and foam sheets of polymers such as soft vinyl chloride, polyethylene and polyurethane.

Amount of the compound of the present invention to be contained in the aforementioned pharmaceutical preparations varies depending on various conditions such as dosage form, route of administration and dosage regimen, so that the amount cannot be defined in a wholesale manner and should be selected from a broad range for each case, but the pharmaceutical preparations may contain the compound generally in an amount of approximately from 1 to 70% by weight.

Administration methods of the aforementioned pharmaceutical preparations, such as intestinal application, oral administration, rectal administration, buccal application and percutaneous absorption, are not particularly limited but optionally decided depending, for example, on the dosage form, the age, sex and other conditions of each patient and the degree of symptoms of each patient. For example, in the case of tablets, pills, solutions, suspensions, emulsions, granules and capsules, they are orally administered, and suppositories are used by rectal administration. In the case of injections, they are administered by intravenous injection as such or after mixing with a usual replacement solution such as of glucose or amino acids or, as occasion demands, administered alone by intraarterial infusion, intramuscular injection, intracutaneous injection, subcutaneous injection or intraperitoneal injection. Ointments are applied, for example, to the skin or oral mucous membrane.

Dose of the active ingredient of the pharmaceutical preparations of the present invention is optionally selected based on the application method, the age, sex and morbid state of each patient, kind of the compound of the present invention to be administered and other conditions, but it may be within the range of generally from 0.1 to 1,000 mg/kg/day, preferably from 0.5 to 500 mg/kg/day. These pharmaceutical preparations of the present invention can be administered by dividing the daily dose recited above into 1 to 4 doses per day.

BEST MODE OF CARRYING OUT INVENTION

Figure 1:
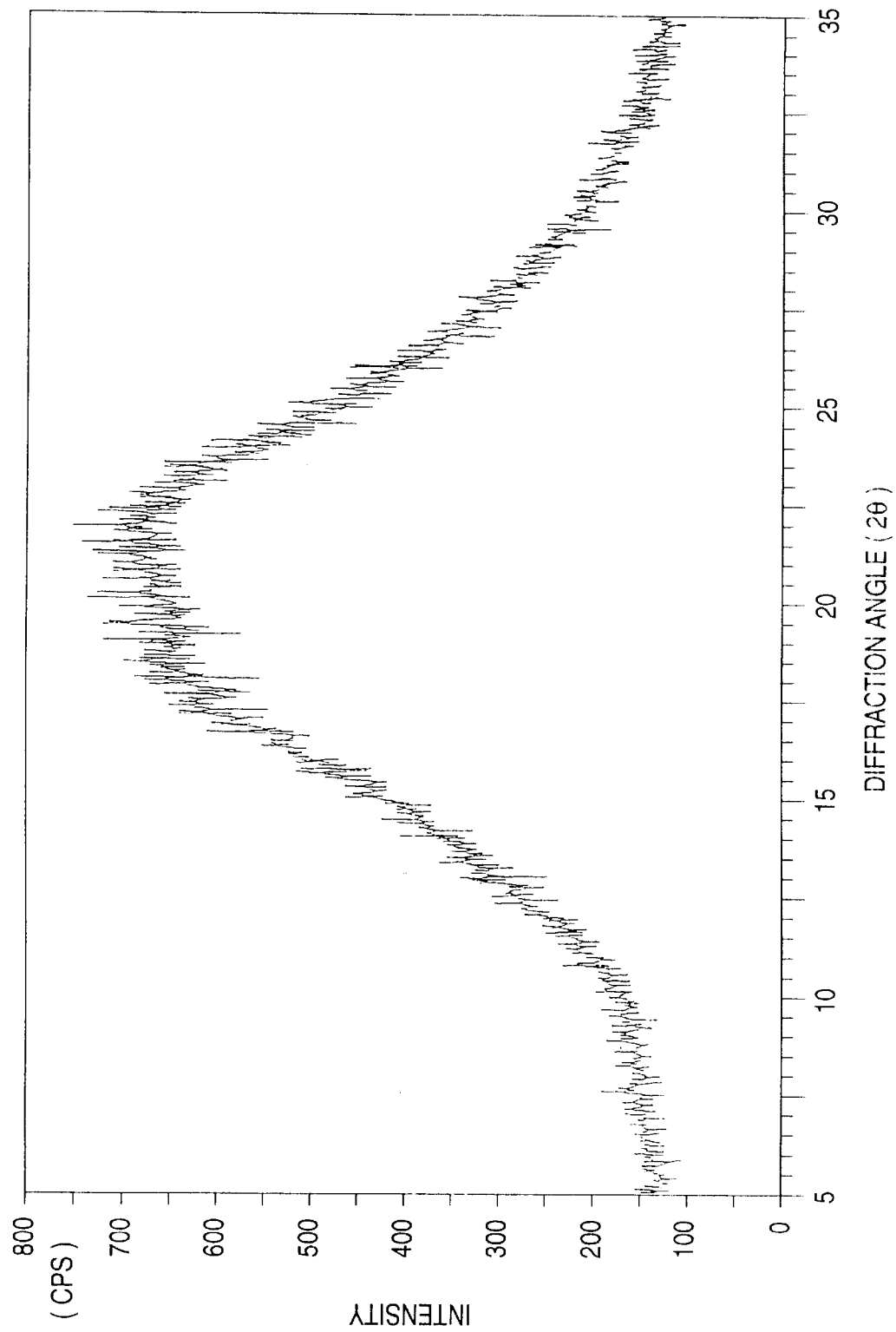
FIG. 1 is a graph showing powder X-ray diffraction of the compound 1-b obtained in Inventive Example 1b.

The following illustratively describes the present invention on novel compounds among the compounds represented by the formula (1), with reference to reference, inventive and test examples, though the invention is not restricted thereby.

REFERENCE EXAMPLE 1

Synthesis of 5-(1,2,4-triazol-1-yl)-2-Nitroaniline

A 10.0 g portion of 5-chloro-2-nitroaniline, 8.0 g of 1,2,4-triazole and 16.0 g of potassium carbonate were suspended in 50 ml of DMF and stirred for 5hours while heating at 130° C. The reaction solution was poured into ice water, and the thus precipitated crystals were collected by filtration and washed with purified water. By washing the crystals with methanol, 10.0 g (84% in yield) of the title compound was obtained. Its physical property values are shown below.

m.p. 259–261° C.

$^1$H-NMR (DMSO-$d_6$): δ (ppm) 7.18 (1 H, dd, J=2.3, 9.4 Hz), 7.55 (1 H, d, J=2.3 Hz), 7.69 (2 H, br-s), 8.15 (1 H, d, J=9.2 Hz), 8.30 (1 H, s), 9.37 (1 H, s)

REFERENCE EXAMPLE 2

Synthesis of 4-(1,2,4-triazol-1-yl)-o-phenylenediamine (1) A 20.0 g portion of 5-(1,2,4-triazol-1-yl)-2-nitroaniline obtained by the method of Reference Example 1 was suspended in 400 ml of methanol, and the suspension was mixed with 5.0 g of 10% palladium-carbon catalyst and subjected to hydrogenation using a Parr type reducing apparatus. When absorption of hydrogen was completed, the reaction solution was mixed with activated carbon and filtered through Celite. The solvent was evaporated from the resulting filtrate, the thus obtained residue was mixed with ethyl acetate and then the thus formed crystals were collected by filtration, thereby obtaining 14.0 g (82% in yield) of the title compound. Its physical property values are shown below.

m.p. 180–182° C.

$^1$H-NMR (DMSO-$d_6$): δ (ppn) 4.72 (2 H, br-s), 4.82 (2 H, br-s), 6.57 (1 H, d, J=8.3 Hz), 6.77 (1 H, dd, J=2.5, 8.3 Hz), 6.92 (1 H, d, J=2.5 Hz), 8.07 (1 H, s), 8.89 (1 H, s)

(2) A 49.5 g portion of 5-(1,2,4-triazol-1-yl)-2-nitroaniline obtained by the method of Reference Example 1 was suspended in 250 ml of 95% ethanol, and the suspension was mixed with 37.0 ml of 5 mol/l sodium hydroxide aqueous solution and heated to 80° C. Next, a total it of 54.0 g of zinc powder was added thereto in 5 g portions at intervals of 10 minutes. After 1 hour of heating under reflux, the reaction mixture was filtered through Celite while it was hot, and then the resulting filtrate was cooled.

Thereafter, the thus precipitated crystals were collected by filtration and washed with cold ethanol to obtain 37.6 g (89% in yield) of the title compound. Its physical property values coincided with the aforementioned data.

(3) A 20.5 g portion of 5-(1,2,4-triazol-1-yl)-2-nitroaniline obtained by the method of Reference Example 1 was suspended in 200 ml of methanol, and the suspension was mixed with 2.2 g of activated carbon and 160 mg of ferric chloride hexahydrate and refluxed for 15 minutes. Next, to this was added dropwise 15 g of 85% hydrazine monohydrate while continuing the reflux. After 2 hours of reflux, insoluble matter was removed by Celite filtration, the solvent was evaporated from the filtrate, ethyl acetate was added to the resulting residue and then the thus formed crystals were collected by filtration to obtain 16.4 g (94% in yield) of the title compound. Its physical property values coincided with the aforementioned data.

INVENTIVE EXAMPLE 1a

Synthesis of 2-(3-isopropoxy-4-methoxyphenyl)-5-(1,2,4-triazol-1-yl)benzimidazole [Compound 1-a]

(1) A 5.98 g portion of a known compound 3-isopropoxy-4-methoxybenzaldehyde was added to 4.49 g of 4-(1,2,4-triazol-1-yl)-o-phenylenediamine obtained in Reference Example 2, and the mixture was stirred for 18 hours in 37 ml of nitrobenzene while heating at 150° C. After cooling, nitrobenzene was evaporated under a reduced pressure. By crystallizing the resulting residue with ethyl acetate/hexane, 4.90 g (55%) of the title compound was obtained. Its physical property values are shown as the Compound No. 1 in Table 1.

(2) Under reflux, 20 ml of methanol solution containing 4.27 g of 3-isopropoxy-4 -methoxybenzaldehyde and 10.81 g of ferric chloride hexahydrate was added dropwise to 35 ml of methanol solution containing 3.50 g of 4-(1,2,4-triazol-1-yl)-o-phenylenediamine obtained in Reference Example 2. The resulting mixture was refluxed for 1 hour and then cooled, and the insoluble matter was collected by filtration. This was suspended in ethyl acetate/water and alkalified with liquid ammonia, and then the insoluble matter was removed by Celite filtration. The ethyl acetate layer was collected and dried over magnesium sulfate, and then the solvent was evaporated. By crystallizing the resulting residue with ethyl acetate/hexane, 4.92 g (70%) of the title compound was obtained. Its physical property values coincided with the data obtained in the above step (1).

(3) A mixture consisting of 1.75 g of 4-(1,2,4-triazol-1-yl)-o-phenylenediamine obtained in Reference Example 2, 1.56 g of sodium hydrogen sulfite and 17 ml of dimethylacetamide was heated to 150° C., to which was subsequently added dropwise 17 ml of dimethylacetamide solution containing 1.94 g of 3-isopropoxy-4-methoxybenzaldehyde. After 2 hours of the reaction at the same temperature, the solvent was evaporated under a reduced pressure. The resulting residue was shaken in ethyl acetate and 10% sodium carbonate aqueous solution to effect separation of layers, and the resulting ethyl acetate layer was collected. The ethyl acetate layer was dried with magnesium sulfate, and then the solvent was evaporated. By crystallizing the resulting residue with ethyl acetate/hexane, 2.37 g (80%) of the title compound was obtained. Its physical property values coincided with the data obtained in the above step (1).

INVENTIVE EXAMPLE 1b

Synthesis of Amorphous 2-(3-isopropoxy-4-methoxyphenyl)-5-(1,2,4-triazol-1-yl)benzimidazole [Compound 1-b]

A 20 g portion of the title compound obtained by the just described production method was suspended in 100 ml of water and heated to 80° C. Next, this was dissolved by adding 70 ml of methanol and cooled to room temperature, and then the resulting precipitate was collected by filtration. This was air-dried and then heat-dried on phosphorus pentoxide under a reduced pressure to obtain 18.37 g (92%) of the title compound. Its physical property values are shown below. Also, its powder X-ray diffraction is shown in FIG. 1, which confirmed that the thus obtained compound is amorphous.

m.p. 118–126° C.

Elemental analysis data for $C_{19}H_{19}N_5O_2 \cdot H_2O$:

|  | H | C | N |
| --- | --- | --- | --- |
| Calcd. | 5.54 | 64.54 | 19.84 |
| Found | 5.49 | 64.53 | 20.02 |

INVENTIVE EXAMPLE 2

Synthesis of 2-(3-cyclopentyloxy-4-methoxyphenyl)-5-(1,2,4-triazol-1-yl)benzimidazole [Compound 2]

The procedure of Inventive Example 1a-(1) was repeated, except that 1.00 g of 3-cyclopentyloxy-4-methoxybenzaldehyde was used instead of 3-isopropoxy-4-methoxybenzaldehyde, thereby obtaining 722 mg (34%) of the title compound. Its physical property values are shown in Table 1.

INVENTIVE EXAMPLE 3

Synthesis of 2-(4-cyclopentyloxy-3-methoxyphenyl)-5-(1,2,4-triazol-1-yl)benzimidazole [Compound 3]

The procedure of Inventive Example 1a-(1) was repeated, except that 2.00 g of 4-cyclopentyloxy-3-methoxybenzaldehyde was used instead of 3-isopropoxy-4-methoxybenzaldehyde, thereby obtaining 1.46 g (34%) of the title compound. Its physical property values are shown in Table 1.

INVENTIVE EXAMPLE 4

Synthesis of 2-(3,4-dimethoxyphenyl)-5-(1,2,4-triazol-1-yl)benzimidazole [Compound 4]

The procedure of Inventive Example 1a-(1) was repeated, except that 949 mg of veratraldehyde was used instead of 3-isopropoxy-4-methoxybenzaldehyde, thereby obtaining 523 mg (28%) of the title compound. Its physical property values are shown in Table 1.

INVENTIVE EXAMPLE 5

Synthesis of 2-(4-methoxy-3-n-pentyloxyphenyl)-5-(1,2,4-triazol-1-yl)benzimidazole [Compound 5]

The procedure of Inventive Example 1a-(1) was repeated, except that 1.37 g of 4-methoxy-3-n-pentyloxybenzaldehyde was used instead of 3-isopropoxy-4-methoxybenzaldehyde, thereby obtaining 2.27 g (53%) of the title compound. Its physical property values are shown in Table 1.

INVENTIVE EXAMPLE 6

Synthesis of 2-(3,4-dimethoxyphenyl)-6-methoxy-5-(1,2,4-triazol-1-yl)benzimidazole [Compound 6]

A 1.06 g portion of 4-(1,2,4-triazol-1-yl)-5methoxy-o-phenylenediamine obtained in the same manner as described in Reference Examples 1 and 2 was allowed to react with 949 mg of veratraldehyde by the method of Inventive Example 1a-(1), thereby obtaining 454 mg (25%) of the title compound. Its physical property values are shown in Table 1.

INVENTIVE EXAMPLES 7 TO 21

Each compound of the Compound Nos. 7 to 21 described in Table 1 was synthesized by the same method of Inventive Example 1a-(3), with their physical property values also shown in Table 1.

INVENTIVE EXAMPLES 22 TO 26

Each compound of the Compound Nos. 23 to 27 described in Table 1 was synthesized by the same method of Inventive Example 1a-(3), with their physical property values also shown in Table 1.

INVENTIVE EXAMPLE 27

2-{3-(2-Cyclohexenyloxy)-4-methoxyphenyl}-5-(1,2,4-triazol-1-yl)benzimidazole [Compound 22]

The title compound having low melting point was obtained from the high melting point compound obtained in Inventive Example 14, in accordance with the method of Inventive Example 1b. Its physical property values are shown in Table 1.

INVENTIVE EXAMPLE 28

Resolution of Optically Active Substances of 2-[3-(2-cyclohexenyloxy)-4-methoxyphenyl]-5-(1,2,4-triazol-1-yl) benzimidazole [Compound 14]

Using an optically active column, the compound 14 was fractionated by HPLC under the following conditions. As a result, (R)-isomer of the compound 14 was obtained by collecting fractions at a retention time of about 35 minutes. Also, its (S)-isomer was obtained by collecting fractions at a retention time of about 40 minutes.

Column: CHIRALPAK AD (mfd. by Daicel Chemical Industries)

Developing solvent: n-hexane/denatured ethanol=90/10

Flow rate: 1.0 ml/min (L-6200 Intelligent Pump (mfd. by Hitachi Ltd.) was used)

Temperature: 40° C.

Detection: UV 254 nm (L-4000 UV Detector (mfd. by Hitachi Ltd.) was used)

TABLE 1

| Comp. No. | Structure | Melting Point and NMR Chemical Shift Value |
|---|---|---|
| 1 | 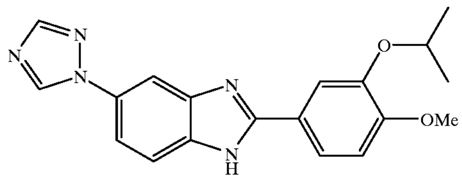 | m.p. 187–188° C.<br>$^1$H-NMR(DMSO-$d_6$):δ(ppm)<br>1.34(6H, d, J=6.1Hz), 3.85(3H, s), 4.68(1H, m), 7.16(1H, d, J=7.0Hz), 7.66–7.79(4H, m), 8.00(1H, br-s), 8.23(1H, s), 9.28(1H, s), 13.00(1H, br) |
| 2 | 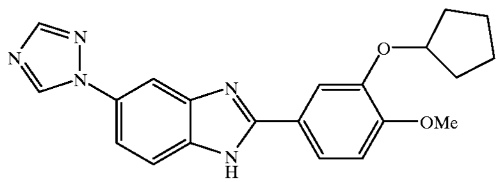 | m.p. 122–127° C.<br>$^1$H-NMR(CDCl$_3$):δ(ppm)<br>1.55(2H, br-s), 1.79–1.86(6H, m), 3.89(3H, s), 4.79(1H, br-s), 6.94(1H, d, J=8.3Hz), 7.52–7.86(5H, m), 8.12(1H, s), 8.55(1H, s) |
| 3 | 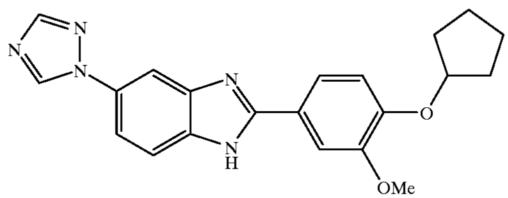 | m.p. 194–196° C.<br>$^1$H-NMR(CDCl$_3$):δ(ppm)<br>1.60–1.98(8H, m), 3.86(3H, s), 4.83(1H, m), 6.95(1H, d, J=8.3Hz), 7.52–8.00(5H, m), 8.13(1H, s), 8.55(1H, s) |
| 4 | 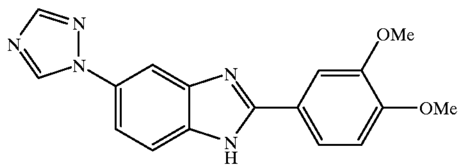 | m.p. 213–215° C.<br>$^1$H-NMR(DMSO-$d_6$):δ(ppm)<br>3.86(3H, s), 3.90(3H, s), 7.16(1H, d, J=8.3Hz), 7.64–7.80(4H, m), 7.90(0.5H, br-s), 8.10(0.5H, br-s), 9.28(1H, d, J=17Hz), 13.04(1H, br) |
| 5 | 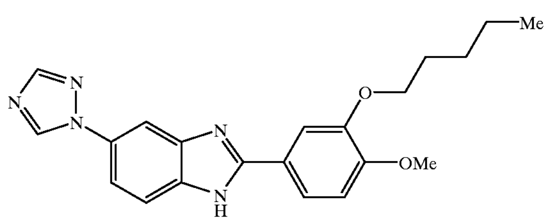 | m.p. 185–187° C.<br>$^1$H-NMR(DMSO-$d_6$):δ(ppm)<br>0.92(3H, t, J=7.1Hz), 1.35–1.50(4H, m), 1.76–1.87(2H, m), 3.86(3H, s), 4.05–4.10(2H, m), 7.16(1H, d, J=8.9Hz) 7.67(1H, dd, J=1.7, 8.6Hz), 7.70(4H, d, J=8.7Hz), 7.76–7.78(2H, m), 8.23(1H, s), 9.28(1H, s), 13.01.(1H, br) |
| 6 | 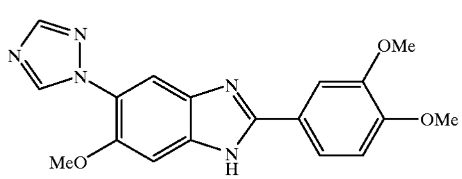 | m.p. 242–246° C.<br>$^1$H-NMR(DMSO-$d_6$):δ(ppm)<br>3.33(3H, s), 3.85(3H, s), 3.89(3H, s), 7.14(1H, d, J=8.3Hz), 7.35(1H, br-s), 7.72–7.76(3H, m), 8.19(1H, s), 8.87(1H, s), 12.89(1H, br) |
| 7 | 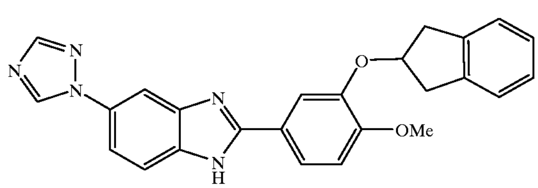 | m.p. 134–136° C.<br>$^1$H-NMR(DMSO-$d_6$)δ(ppm):<br>13.05(1H, br), 9.29(1H, s), 8.24(1H, s), 8.00(1H, s), 7.85–7.69(4H, m), 7.32–7.28(2H, m), 7.23–7.15(3H, m), 5.34(1H, m), 3.80(3H, s), 3.45(2H, dd, J=17.2, 5.9Hz), 3.12(2H, dd, J=17.2, 2.3Hz) |

TABLE 1-continued

| Comp. No. | Structure | Melting Point and NMR Chemical Shift Value |
|---|---|---|
| 8 | 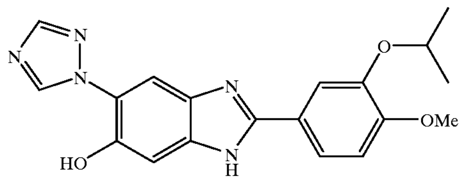 | m.p. 163–167° C.<br>$^1$H-NMR(DMSO-d$_6$)δ(ppm):<br>12.75(1H, br), 10.20(1H, s), 8.92(1H, s),<br>8.18(1H, s), 7.71–7.68(3H, m), 7.19(1H, s),<br>7.13(1H, d, J=9.2Hz), 4.67(1H, m), 3.83(3H,<br>s), 1.32(6H, d, J=5.9Hz) |
| 9 | 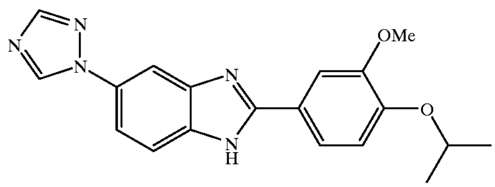 | m.p. 185–186° C.<br>$^1$H-NMR(DMSO-d$_6$)δ(ppm):<br>9.29(1H, s), 8.24(1H, s), 8.01(1H, br-s),<br>7.80–7.65(4H, m), 7.16(1H, d, J=9.0Hz),<br>4.69(1H, m), 3.89(3H, s), 1.31(6H, d,<br>J=6.3Hz) |
| 10 | 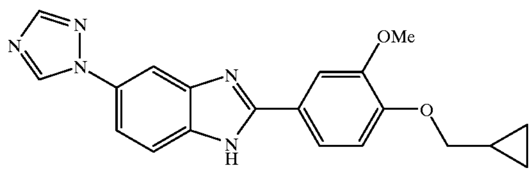 | m.p. 118–120° C.<br>$^1$H-NMR(DMSO-d$_6$)δ(ppm):<br>13.04(1H, br), 9.29(1H, s),8.24(1H, s),<br>8.00(1H, br), 7.80–7.69(4H, m), 7.11(1H, d,<br>J=8.6Hz), 3.91(3H, s), 3.90(2H, d,<br>J=6.9Hz), 1.27(1H, m), 0.64–0.57(2H, m),<br>0.38–0.32(2H, m) |
| 11 | 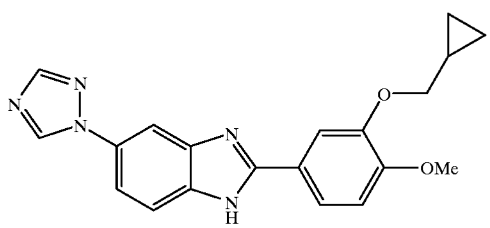 | m.p. 193–194° C.<br>$^1$H-NMR(DMSO-d$_6$)δ(ppm):<br>13.01(1H, br), 9.28(1H, s), 8.24(1H, s),<br>7.99(1H, br), 7.79–7.68(4H, m), 7.16(1H, d,<br>J=8.4Hz), 3.93(2H, d, J=6.9Hz), 3.87(3H, s),<br>1.30(1H, m), 0.66–0.59(2H, m),<br>0.41–0.37(2H, m) |
| 12 | 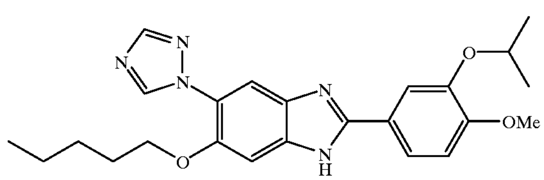 | m.p. 161–164° C.<br>$^1$H-NMR(DMSO-d$_6$)δ(ppm):<br>12.85(1H, br), 8.84(1H, s), 9.19(1H, s),<br>7.75(2H, s), 7.73(1H, s), 7.34(1H, br),<br>7.14(1H, d, J=8.9Hz). 4.67(1H, m),<br>4.09(2H, t, J=6.3Hz), 3.84(3H, s),<br>1.70(2H, m), 1.33(6H, d, J=6.1Hz),<br>1.32(4H, m), 0.86(3H, t, d=6.7Hz) |
| 13 | 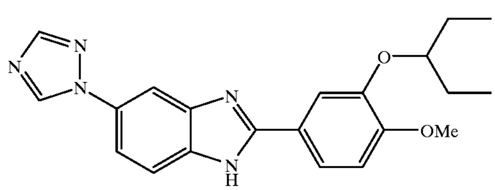 | m.p. 143–146° C.<br>$^1$H-NMR(DMSO-d$_6$)δ(ppm):<br>13.01(1H, br), 9.28(1H, s), 8.24(1H, s),<br>8.00(1H, br), 7.79–7.67(4H, m), 7.16(1H,<br>d, J=8.9Hz), 4.32(1H, m), 3.86(3H, s),<br>1.99–1.63(4H, m), 0.98–0.92(6H, m) |
| 14 | 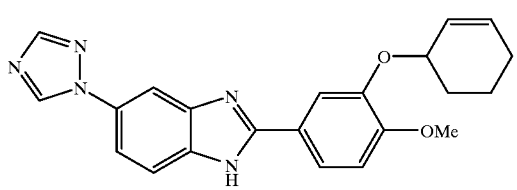 | m.p. 194–195° C.<br>$^1$H-NMR(DMSO-d$_6$)δ(ppm):<br>13.0(1H, br), 9.28(1H, s), 8.23(1H, s),<br>7.99(1H, br), 7.81–7.65(4H, m), 7.17(1H,<br>d, J=8.2Hz), 6.00–5.86(2H, m), 4.93(1H,<br>m), 3.85(3H, s), 2.06–1.65(6H, m) |

TABLE 1-continued

| Comp. No. | Structure | Melting Point and NMR Chemical Shift Value |
|---|---|---|
| 15 | 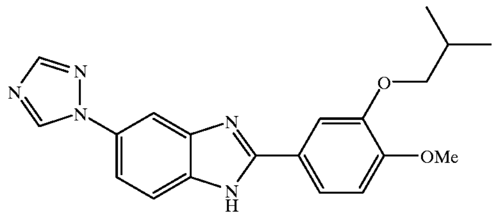 | m.p. 201° C.<br>$^1$H-NMR(DMSO-d$_6$)δ(ppm):<br>13.02(1H, br), 9.28(1H, s), 8.24(1H, s),<br>7.98(1H, br), 7.80–7.77(4H, m), 7.15(1H,<br>m)3.86(3H, s), 3.86(2H, d, J=6.8Hz),<br>2.10(1H, m), 1.03(6H, d, J=6.6Hz) |
| 16 | 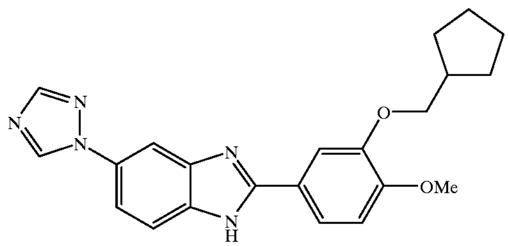 | m.p. 204–206° C.<br>$^1$H-NMR(DMSO-d$_6$)δ(ppm):<br>13.02(1H, br), 9.28(1H, s), 8.23(1H, s),<br>7.99(1H, br), 7.79–7.66(4H, m),<br>7.15(1H, m), 3.86(3H, s), 2.38(1H, m),<br>1.85–1.80(2H, m), 1.76–1.54(4H, m),<br>1.43–1.36(2H, m) |
| 17 | 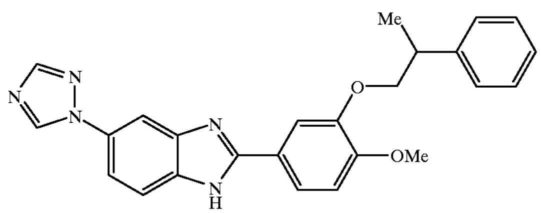 | m.p.191–192° C.<br>$^1$H-NMR(DMSO-d$_6$)δ(ppm):<br>13.00(1H, br), 9.27(1H, s), 8.23(1H, s),<br>8.00(1H, br), 7.81–7.68(4H, m), 7.43–7.22(4H,<br>m), 7.45(1H, d, J=9.0Hz), 4.22(1H, m),<br>3.84(3H, s), 3.29(1H, m), 1.39(3H, d,<br>J=7.1Hz) |
| 18 | 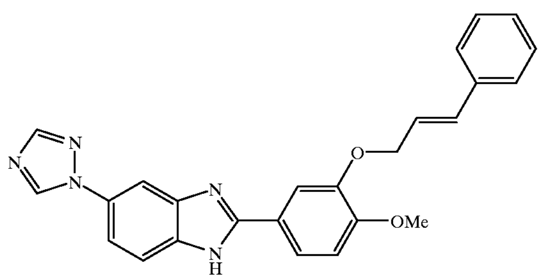 | m.p. 214–216° C.<br>$^1$H-NMR(DMSO-d$_6$)δ(ppm):<br>13.04(1H, br), 9.29(1H, s), 8.24(1H, s),<br>8.00(1H, br), 7.87–7.18(10H, m), 6.83(1H, d,<br>J=16.0Hz), 6.58(1H, td, J=16.0, 5.9Hz),<br>4.84(2H, d, J=5.4Hz), 3.88(3H, s) |
| 19 | 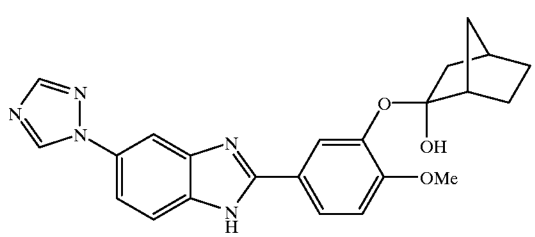 | m.p. 232–234° C.<br>$^1$H-NMR(DMSO-d$_6$)δ(ppm):<br>13.01(1H, br-s), 9.29(1H, s), 8.24(1H, s),<br>8.01(1H, br-s), 7.78–7.66(4H, m), 7.15(1H, d,<br>J=8.6Hz), 4.36(1H, d, J=6.1Hz), 3.84(3H,<br>s), 2.44(1H, br-s), 2.32(1H, s),<br>1.90–1.87(2H, m), 1.66–1.44(4H, m),<br>1.27–1.15(3H, m) |
| 20 | 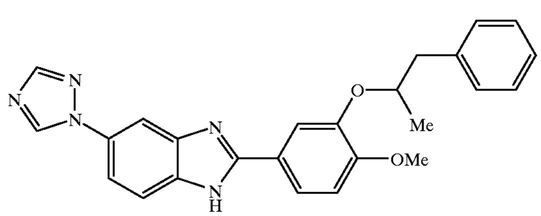 | m.p. 101–105° C.<br>$^1$H-NMR(DMSO-d$_6$)δ(ppm):<br>13.00(1H, br), 9.28(1H, s), 8.23(1H, s),<br>8.00(1H, br), 7.80–7.68(4H, m), 7.36–7.15(6H,<br>m), 4.77(1H, m), 3.85(3H, s), 3.09(1H,<br>dd, J=13.7, 6.3Hz), 2.91(1H, dd, J=13.5,<br>6.3Hz), 1.27(3H, d, J=5.9Hz) |

TABLE 1-continued

| Comp. No. | Structure | Melting Point and NMR Chemical Shift Value |
|---|---|---|
| 21 | 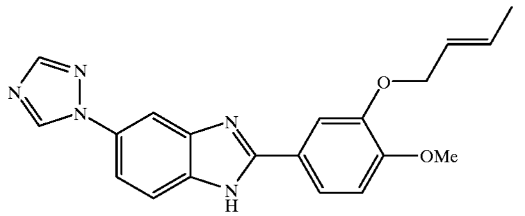 | m.p. 197–199° C.<br>$^1$H-NMR(DMSO-d$_6$)δ(ppm):<br>13.02(1H, br-s), 9.29(1H, s), 8.25(1H, s),<br>8.01(1H, br), 7.82–7.67(4H, m),<br>7.15(1H, d, J=8.6Hz), 5.52(1H, m), 4.63(1H,<br>d, J=6.8Hz), 3.85(3H, s), 1.77(6H, d,<br>J=5.1Hz) |
| 22 | 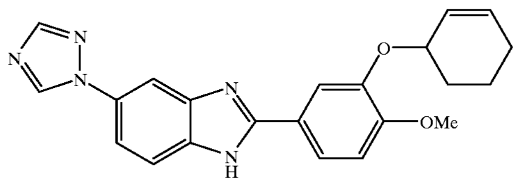 | m.p. 122–123° C.<br>$^1$H-NMR(DMSO-d$_6$)δ(ppm):<br>13.01(1H, d, J=8.2Hz), 9.28(1H, d,<br>J=10.7Hz), 8.24(1H, d, J=4.9Hz),<br>8.10–7.63(4H, m), 7.17(1H, d, J=8.2Hz),<br>5.97(1H, dt, J=7.1, 3.2Hz), 5.88(1H, m),<br>4.93(1H, br-s), 3.85(3H, s), 2.08–1.61(6H, m) |
| 23 | 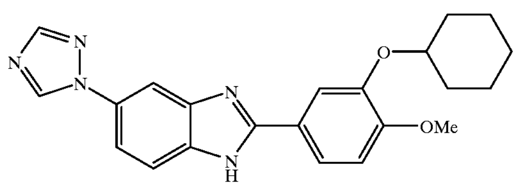 | m.p. 197–198° C.<br>$^1$H-NMR(DMSO-d$_6$)δ(ppm):<br>13.01(1H, br), 9.28(1H, s), 8.24(1H, s),<br>8.01(1H, br), 7.80–7.65(4H, m),<br>7.17(1H, d, J=9.1Hz), 4.39(1H, m), 3.85(3H,<br>s), 1.99(2H, m), 1.55(2H, m), 1.78–1.30(6H, m) |
| 24 | 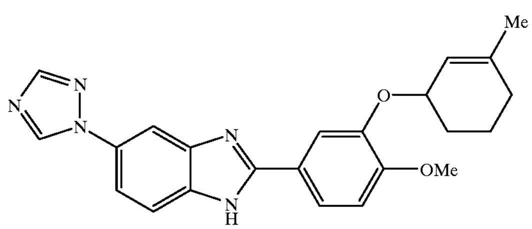 | m.p. 135–140° C.<br>$^1$H-NMR(DMSO-d$_6$)δ(ppm):<br>13.01(1H, br), 9.28(1H, s), 8.24(1H, s),<br>8.01(1H, br), 7.81–7.69(4H, m), 7.16(1H, d,<br>J=8.4Hz), 5.64(1H, br-s), 4.93(1H, br),<br>3.85(3H, s), 2.00–1.63(6H, m), 1.72(3H, m) |
| 25 | 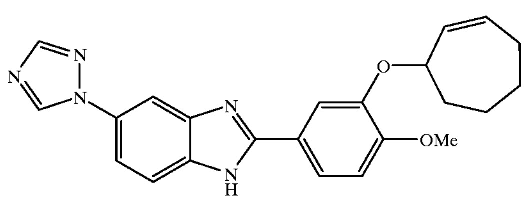 | m.p. 188–189° C.<br>$^1$H-NMR(DMSO-d$_6$)δ(ppm):<br>13.02(1H, br), 9.29(1H, s), 8.24(1H, s),<br>8.00(1H, br), 7.80–7.67(4H, m),<br>7.18(1H, d, J=8.6Hz), 5.95–5.78(2H, m),<br>5.08(1H, m), 3.86(3H, s), 2.27–2.19(2H,<br>m), 2.04–2.02(2H, m), 1.80–1.69(3H, m),<br>1.40–1.35(1H, m) |
| 26 | 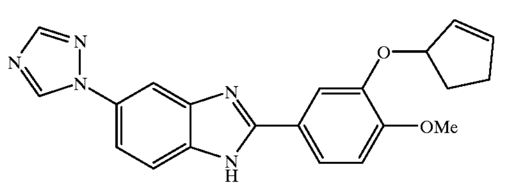 | m.p. 140–144° C.<br>$^1$H-NMR(DMSO-d$_6$)δ(ppm):<br>13.03(1H, br), 9.29(1H, s), 8.24(1H, s),<br>8.02(1, br), 7.82–7.68(4H, m), 7.16(1H, d,<br>J=8.4Hz), 6.20(1H, m), 6.04(1H, m),<br>5.49(1H, br-s), 3.99(3H, s), 2.54–2.37(3H,<br>m), 1.92–1.85(1H, m) |
| 27 | 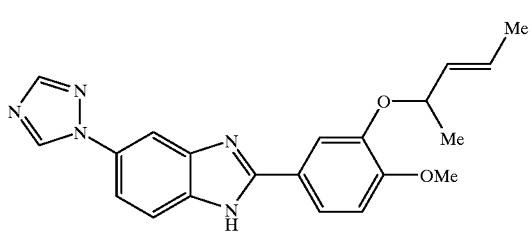 | m.p. 132–134° C.<br>$^1$H-NMR(DMSO-d$_6$)δ(ppm):<br>12.98(1H, br), 9.28(1H, s), 8.23(1H s),<br>8.00(1H, br), 7.81–7.67(4H, m), 7.15(1H,<br>d, J=9.0Hz), 5.80–5.57(2H, m), 4.97(1H,<br>m), 3.85(3H, s), 1.64(3H, d, J=6.4Hz),<br>1.40(3H, d, 6.1Hz) |

In the above table, "Me" means a methyl group.

COMPARATIVE EXAMPLES

The following control compounds 1 to 5 were synthesized and used in pharmacological tests.

Control Compound 1:

Control Compound 2:

Control Compound 3:

Control Compound 4:

Control Compound 5:

(1) Each of the control compounds 1 to 3 was synthesized in accordance with the method described in JP-A-3-14579. Their physical property values are shown in the following.

(2) Each of the control compounds 4 and 5 was synthesized in accordance with the method described in International Publication No. WO 94/12461. Their physical property values are shown below.

Control Compound 1
  m.p. 264–266° C.
  $^1$H-NMR (DMSO-$d_6$): δ (ppm) 7.77–7.86 (2 H, m), 8.12–8.14 (3 H, m), 8.26 (1 H, s), 8.79–8.81 (2 H, m), 9.34 (1 H, s)

Control Compound 2
  m.p. 230–232° C.
  H-NMR (DMSO-$d_6$): δ (ppm) 3.88 (3 H, s), 4.05 (3 H, s), 6.73–6.79 (2 H, m), 7.64–7.72 (2 H, m), 8.04 (1 H, brs), 8.04–8.31 (2 H, m)r, 9.27 (1 H, s)

Control Compound 3
  m.p. 189–190° C.
  $^1$H-NMR (DMSO-$d_6$) δ (ppm) 3.87 (3 H, s), 4.04 (3 H, s), 6.72–6.79 (2 H, m), 7.11 (1 H, s), 7.39–7.42 (1 H, m), 7.71–7.84 (3 H, m), 8.20–8.29 (2 H, m)

Control Compound 4
  m.p. 244–246° C.
  1H-NMR (DMSO-$d_6$): δ (ppm) 1.62–2.00 (8 H, m), 3.84 (3 H, s), 4.90–4.95 (1 H, m), 7.14–7.17 (1 H, m), 7.62–8.19 (5 H, m)

Control Compound 5
  m.p. 253–256° C.
  $^1$H-NMR (DMSO-$d_6$): δ (ppm) 3.07–3.17 (2 H, m)r, 3.49–3.58 (2 H, m)), 3.84 (3 H, s), 5.39–5.43 (1 H, m), 7.18–7.32 (5 H, m), 7.82–8.09 (4 H, m)), 8.27 (1 H, s)

TEST EXAMPLE 1

Interleukin-4 (IL-4) Production Inhibitory Activity

This test was carried out in accordance with the method of Shelby et al. (J. Allergy Clin. Immunol., Vol. 100, No. 4, 511–519 (1997)). That is, CD4$^+$T cells were purified from mouse spleen cells and suspended in 10% FCS-containing RPMI 1640 culture medium, and the cell suspension was inoculated into wells of a 24 well culture plate, which had been coated with anti-rat IgG, at a density of 3×10$^6$ cells per well. Anti-mouse CD3 antibody and anti-mouse CD28 antibody were added thereto, and the cells were cultured at 37° C. for 3 days in an atmosphere of 5% $CO_2$. The thus grown cells were recovered, washed three times with HBSS (Hank's balanced salt solution) and then suspended in 10% FCS-containing RPMI 1640 culture medium. The cell suspension was inoculated into wells of a 24 well culture plate at a density of 1×10$^6$ cells per well, mixed with IL-2 and cultured for additional 3 days. The resulting cells were recovered, washed three times with HBSS and then suspended in 10% FCS-containing RPMI 1640 culture medium. The cell suspension was inoculated into wells of a 24 well culture plate, which had been coated with anti-rat IgG, at a density of 2×10$^6$ cells per well, anti-mouse CD3 antibody and anti-mouse CD28 antibody were added thereto, and the cells were again cultured for 1 day. The culture supernatant was recovered from each well to measure the amount of produced IL-4 by ELISA. Each drug to be tested was treated at the time of the second addition of anti-mouse CD3 antibody and anti-mouse CD28 antibody to calculate its inhibition percentage based on the control IL-4 production by the addition of the solvent alone, and $IC_{50}$ (50% inhibition concentration) of each drug to be tested was calculated based on the regression line. The results are shown in Table 2.

TEST EXAMPLE 21

Phosphodiesterase IV (PDE (IV)) Inhibitory Activity

Purification of PDE (IV) and measurement of its activity were carried out by partially modifying the method of Saeki et al. (Biochem. Pharmacol., Vol. 46, 833–839, 1993). That is, PDE(IV) was purified by centrifuging rat brain homogenate at 105,000×g, applying the resulting supernatant to a Q-Sepharose column and then eluting the protein with a density gradient of 0 to 0.5 M NaCl.

Activity of PDE(IV) was measured by the following two step procedure. Using 3H-cAMP (1 μM in final concentration) as the substrate, the reaction was carried out at 37° C. for 10 minutes in a reaction solution containing tris(hydroxyl)aminomethane (50 mM, pH B8.0), EGTA (0.1 mM) and $MgCl_2$ (0.1 mM) and then the reaction was stopped by incubating the reaction solution at 95° C. for 5 minutes. The thus formed 5'-AMP was hydrolyzed with 5'-nucleotidase, and AG1 X-8 resin was added thereto to effect adsorption of unreacted CAMP. After centrifugation, 3H-adenosine was counted using a scintillation counter. Each of the drugs to be tested (compounds 1, 2 and 4) was added at the time of the commencement of reaction to calculate its inhibition percentage based on the control in which the solvent alone was added, and $IC_{50}$ (50% inhibition concentration) of each drug to be tested was calculated based on the regression line. The results are shown in Table 2.

TABLE 2

| Compound No. | IL-4 production inhibition $IC_{50}$ (μM) | PDE(IV) inhibition $IC_{50}$ (μM) |
| --- | --- | --- |
| 1 | 4.3 | 0.02 |
| 11 | 5.5 | 1.6 |
| 14 | 6.1 | 0.54 |
| 18 | 5.1 | 0.051 |
| 25 | 2.8 | 0.73 |

TEST EXAMPLE 3
Ear Edema Reaction Inhibitory Activity in Mice [Test Inflammation]

This test was test was carried out in accordance with the method of Sawada et al. (*Clin. Exp. Allergy,* Vol. 27, pp. 225–231, 1996). Each of BALB/c mice was immunized by the intraperitoneal injection of 1 μg of egg albumin which had been adsorbed to 1 mg of ALUM. After 14 days of the immunization, ear edema reaction was induced by intracutaneous injection of 1 μg of egg albumin into mouse earlobe. Ear edema ($\times 10^2$ mm) was calculated by measuring thickness of the ear before and 1 hour after the induction with a dial thickness gage (Peacok). Each of the drugs to be tested (compounds 1 and 2) was suspended in 0.5% hydropropylmethylcellulose (HPMC) solution and orally administered 1 hour before the reaction induction. Ear edema caused by the antigen was calculated by subtracting ear edema after respective time of induction in the case of the same treatment of normal mice, and the ear edema inhibition ratio (%) of the drugs to be tested was calculated based on the solvent-administered (control) group. The results are shown in Table 3.

The same test was carried out on the aforementioned control compounds 1 to 5. The results are also shown in Table 3.

TEST EXAMPLE 4
Antigen-Induced Airway Reactivity Acceleration Inhibitory Activity in Mice [Test on Chronic Inflammation]

The model for this test was prepared out in accordance with the method of Nagai et al. (*Life Sciences,* Vol. 54, pp. 471–475, 1994). Each of BALB/c mice was immunized by the intraperitoneal injection of 1 μg of egg albumin which had been adsorbed to 1 mg of ALUM. After 14 days of the immunization, each animal was exposed to 1% egg albumin solution using an ultrasonic nebulizer, and this treatment was repeated three times at 3 day intervals. After 24 hours of the final exposure, the airway contraction reaction against intravenously injected acetylcholine (30 μg/animal) was measured as overflow volume ($\times 0.01$ ml) by the modified method of Konzett and Rossler under pentobarbital anesthesia. Each of the drugs to be tested (compounds 1 and 2) was suspended in 0.5% HPMC solution and orally administered once a day for a total of 10 days starting from the day before the antigen exposure until the day of final exposure. Accelerated quantity of the airway contraction reaction caused by the antigen exposure was calculated by subtracting the contraction reaction against intravenously injected acetylcholine in the case of the same treatment of normal mice, and the airway reactivity acceleration inhibition ratio (%) of the drugs to be tested was calculated based on the solvent-administered (control) group. The results are shown in Table 3.

The same test was carried out on the aforementioned control compounds 1 to 5. The results are also shown in Table 3.

TABLE 3

| Compound No. | Mouse ear edema reaction inhibition (dose) | Airway reactivity acceleration inhibition (dose) |
| --- | --- | --- |
| Compound 1 | 60% (30 mg/kg) | 58% (10 mg/kg) |
| Compound 2 | 78% (30 mg/kg) | 47% (30 mg/kg) |
| Control compound 1 | 2% (30 mg/kg) | 26% (30 mg/kg) |
| Control compound 2 | 17% (30 mg/kg) | 30% (30 mg/kg) |
| Control compound 3 | 37% (30 mg/kg) | 6% (30 mg/kg) |
| Control compound 4 | 0% (100 mg/kg) | −17% (30 mg/kg) |
| Control compound 5 | 0% (100 mg/kg) | −3% (30 mg/kg) |

Based on the results of the aforementioned Test Examples 1 and 2, it was confirmed that the benzimidazole compound of the present invention has excellent actions of both IL-4 production inhibitory activity and PDE (IV) inhibitory activity.

The compound of the present invention also showed excellent effects in the acute and chronic inflammation tests of Test Examples 3 and 4. However, none of the control compounds 1 to 5 showed excellent effects in these tests.

Next, formulation examples of the compound of the present invention are shown in the following.

| [Formulation Example 1] Tablets | |
| --- | --- |
| Compound 1 | 200 mg |
| Corn starch | 50 mg |
| Microcrystalline cellulose | 50 mg |
| Hydroxypropylcellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Tablets of 400 mg per one tablet having the above blending ratio were prepared in the usual way.

| [Formulation Example 2] Granules | |
| --- | --- |
| Compound 2 | 300 mg |
| Lactose | 540 mg |
| Corn starch | 100 mg |
| Hydroxypropylcellulose | 50 mg |
| Talc | 10 mg |

Granules of 1,000 mg per one package having the above blending ratio were prepared in the usual way.

|  [Formulation Example 3] Capsules ||
|---|---|
| Compound 3 | 200 mg |
| Lactose | 30 mg |
| Corn starch | 50 mg |
| Microcrystalline cellulose | 10 mg |
| Magnesium stearate | 3 mg |

Capsules of 293 mg per one capsule having the above blending ratio were prepared in the usual way.

|  [Formulation Example 4] Injections ||
|---|---|
| Compound 4 | 100 mg |
| Sodium chloride | 3.5 mg |
| Distilled water for injection use (2 ml per one ampoule) | balance |

Injections having the above blending ratio were prepared in the usual way.

|  [Formulation Example 5] Syrups ||
|---|---|
| Compound 5 | 200 mg |
| Purified sucrose | 60 mg |
| Ethyl parahydroxybenzoate | 5 mg |
| Butyl parahydroxybenzoate | 5 mg |
| Perfume | proper amount |
| Coloring agent | proper amount |
| Purified water | balance |

Syrups having the above blending ratio were prepared in the usual way.

|  [Formulation Example 6] Suppositories ||
|---|---|
| Compound 6 | 300 mg |
| Witepsol W-35 | 1,400 mg |

(trade name, a mixture of mono-, di- and tri-glycerides of from lauric acid to stearic acid, manufactured by Dynamite Novel)

Suppositories having the above blending ratio were prepared in the usual way.

INDUSTRIAL APPLICABILITY

As described above, the benzimidazole derivatives of the present invention and a pharmacologically acceptable salt thereof have both of IL-4 production inhibitory activity and PDE (IV) inhibitory activity and are useful as therapeutic and preventive drugs for acute and chronic inflammatory diseases such as atopic dermatitis, allergic rhinitis, bronchial asthma and glomerulonephritis. They are also useful as therapeutic and preventive drugs for autoimmune diseases such as rheumatism and multiple sclerosis, as well as insulin-resistant diabetes and AIDS.

What is claimed is:

1. A benzimidazole derivative compound represented by formula (I):

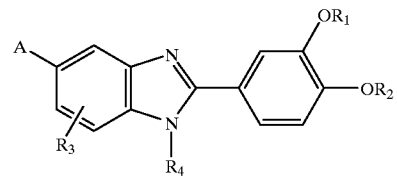

wherein, A represents a triazole group; $R_1$ and $R_2$ may be the same or different from each other and each represents an aliphatic hydrocarbon radical which may have an alicyclic or aromatic hydrocarbon radical or an alicyclic hydrocarbon radical, wherein
said aliphatic hydrocarbon radical may have a substituent group selected from a monocyclic alicyclic hydrocarbon radical having 3 to 7 carbon atoms, which may have a straight- or branched-chain saturated lower alkyl group having 1 to 3 carbon atoms, an alicyclic hydrocarbon radical of cross-linked ring or polycyclic system and a phenyl group, and
said alicyclic hydrocarbon radical is a monocyclic alicyclic hydrocarbon radical having 3 to 7 carbon atoms, which may have a straight- or branched-chain lower alkyl group having 1 to 3 carbon atoms or an alicyclic hydrocarbon radical of cross-linked ring or polycyclic system;
$R_3$ represents a hydrogen atom; and $R_4$ represents a hydrogen atom, or a pharmacologically acceptable salt thereof.

2. The benzimidazole derivative compound or a pharmacologically acceptable salt thereof according to claim 1, wherein A is 1,2,4-triazol-1-yl.

3. The benzimidazole derivative compound or a pharmacologically acceptable salt thereof according to any one of claims 1 to 2, wherein, the aliphatic hydrocarbon radical moiety of said aliphatic hydrocarbon radical which may have an alicyclic or aromatic hydrocarbon radical in $R_1$ or $R_2$ is a straight- or branched-chain lower alkyl group having 1 to 6 carbon atoms or a straight- or branched-chain lower alkenyl group having 2 to 6 carbon atoms.

4. The benzimidazole derivative compound or a pharmacologically acceptable salt thereof according to any one of claims 1 to 2, wherein $R_1$ and $R_2$ may be the same or different from each other and each is a methyl, isopropyl, isopentyl, cyclopropylmethyl, cyclopentylmethyl, benzyl, phenylethyl, phenylpropyl, cinnamyl, cyclopentyl, cyclopentenyl, cyclohexyl, cyclohexenyl or cycloheptenyl group.

5. The benzimidazole derivative compound or a pharmacologically acceptable salt thereof according to claim 1, wherein A is 1,2,4-triazol-1-yl or 1,2,4-triazol-4-yl; $R_1$ and $R_2$ may be the same or different from each other and each is a straight- or branched lower alkyl group having 1 to 6 carbon atoms, which may have a monocyclic alicyclic hydrocarbon radical having 3 to 7 carbon atoms, or a monocyclic alicyclic hydrocarbon radical having 3 to 7 carbon atoms; $R^3$ is a hydrogen atom or a lower alkoxy group; and $R^4$ is a hydrogen atom.

6. The benzimidazole derivative compound or a pharmacologically acceptable salt thereof according to claim 5, wherein A is 1,2,4-triazol-1-yl; $R_1$ and $R_2$ may be the same or different from each other and each is a methyl, isopropyl, isopentyl, cyclopropylmethyl, cyclopentylmethyl, cyclopentyl, cyclopentenyl, cyclohexenyl or cycloheptenyl group; $R_3$ is a hydrogen atom; and $R_4$ is a hydrogen atom.

7. A pharmaceutical composition, comprising an effective amount of the compound of formula (I):

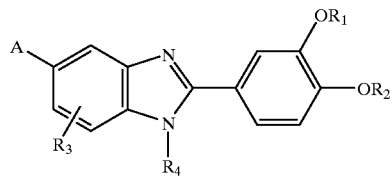

wherein, A represents a triazole group; $R_1$ and $R_2$ may be the same or different from each other and each represents an aliphatic hydrocarbon radical which may have an alicyclic or aromatic hydrocarbon radical or an alicyclic hydrocarbon radical, wherein
said aliphatic hydrocarbon radical may have a substituent group selected from a monocyclic alicyclic hydrocarbon radical having 3 to 7 carbon atoms, which may have a straight- or branched-chain saturated lower alkyl group having 1 to 3 carbon atoms, an alicyclic hydrocarbon radical of cross-linked ring or polycyclic system and a phenyl group, and
said alicyclic hydrocarbon radical is a monocyclic alicyclic hydrocarbon radical having 3 to 7 carbon atoms, which may have a straight- or branched-chain lower alkyl group having 1 to 3 carbon atoms or an alicyclic hydrocarbon radical of cross-linked ring or polycyclic system;
$R_3$ represents a hydrogen atom; and $R_4$ represents a hydrogen atom, or a pharmacologically acceptable salt thereof;
and a pharmacological carrier.

8. A therapeutic agent for acute and chronic inflammatory diseases, comprising an effective amount of the compound of formula (I):

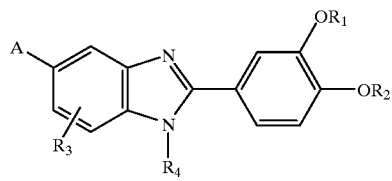

wherein, A represents a triazole group; $R_1$ and $R_2$ may be the same or different from each other and each represents an aliphatic hydrocarbon radical which may have an alicyclic or aromatic hydrocarbon radical or an alicyclic hydrocarbon radical, wherein
said aliphatic hydrocarbon radical may have a substituent group selected from a monocyclic alicyclic hydrocarbon radical having 3 to 7 carbon atoms, which may have a straight- or branched-chain saturated lower alkyl group having 1 to 3 carbon atoms, an alicyclic hydrocarbon radical of cross-linked ring or polycyclic system and a phenyl group, and
said alicyclic hydrocarbon radical is a monocyclic alicyclic hydrocarbon radical having 3 to 7 carbon atoms, which may have a straight- or branched-chain lower alkyl group having 1 to 3 carbon atoms or an alicyclic hydrocarbon radical of cross-linked ring or polycyclic system;
$R_3$ represents a hydrogen atom; and $R_4$ represents a hydrogen atom, or a pharmacologically acceptable salt thereof;
and a pharmacological carrier.

9. An anti-allergic or anti-inflammatory agent, comprising an effective amount of the compound of formula (I):

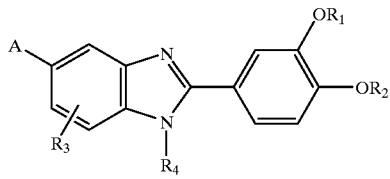

wherein, A represents a triazole group: $R_1$ and $R_2$ may be the same or different from each other and each represents an aliphatic hydrocarbon radical which may have an alicyclic or aromatic hydrocarbon radical or an alicyclic hydrocarbon radical, wherein
said aliphatic hydrocarbon radical may have a substituent group selected from a monocyclic alicyclic hydrocarbon radical having 3 to 7 carbon atoms, which may have a straight- or branched-chain saturated lower alkyl group having 1 to 3 carbon atoms, an alicyclic hydrocarbon radical of cross-linked ring or polycyclic system and a phenyl group, and
said alicyclic hydrocarbon radical is a monocyclic alicyclic hydrocarbon radical having 3 to 7 carbon atoms, which may have a straight- or branched-chain lower alkyl group having 1 to 3 carbon atoms or an alicyclic hydrocarbon radical of cross-linked ring or polycyclic system;
$R_3$ represents a hydrogen atom; and $R_4$ represents a hydrogen atom, or a pharmacologically acceptable salt thereof;
and a pharmacological carrier.

10. A method for treating acute and chronic inflammatory diseases, comprising the step of administering to patients an effective amount of the benzimidazole derivative compound represented by formula (I):

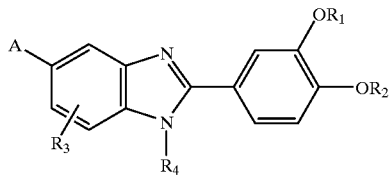

wherein, A represents a triazole group; $R_1$ and $R_2$ may be the same or different from each other and each represents and aliphatic hydrocarbon radical which may have an alicyclic or aromatic hydrocarbon radical or an alicyclic hydrocarbon radical, wherein
said aliphatic hydrocarbon radical may have a substituent group selected from a monocyclic alicyclic hydrocarbon radical having 3 to 7 carbon atoms, which may have a straight- or branched-chain saturated lower alkyl group having 1 to 3 carbon atoms, an alicyclic hydrocarbon radical of cross-linked ring or polycyclic system and a phenyl group, and
said alicyclic hydrocarbon radical is a monocyclic alicyclic hydrocarbon radical having 3 to 7 carbon atoms, which may have a straight- or branched-chain lower alkyl group having 1 to 3 carbon atoms or an alicyclic hydrocarbon radical of cross-linked ring or polycyclic system;
$R_3$ represents a hydrogen atom; and $R_4$ represents a hydrogen atom,
or a pharmacologically acceptable salt thereof.

11. The benzimidazole derivative compound according to claim 1, wherein said derivative is

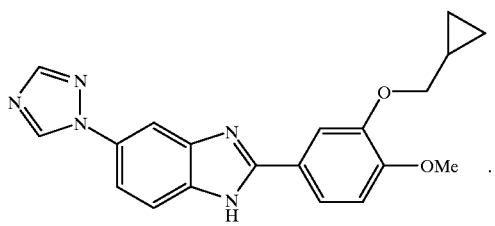

12. The benzimidazole derivative compound according to claim 1, wherein said derivative is

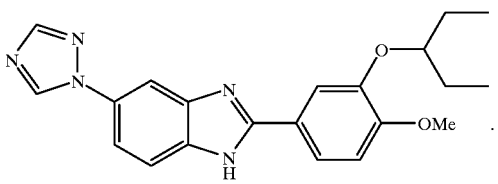

13. The pharmaceutical composition according to claim 7, wherein said compound is

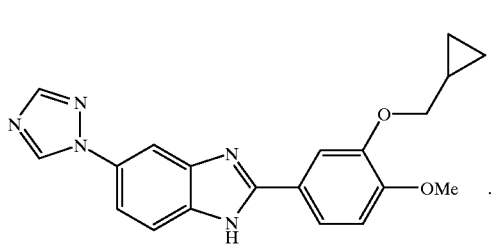

14. The pharmaceutical composition according to claim 7, wherein said compound is

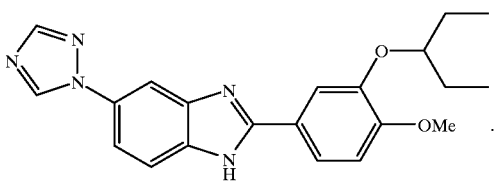

15. The therapeutic agent according to claim 8, wherein said compound is

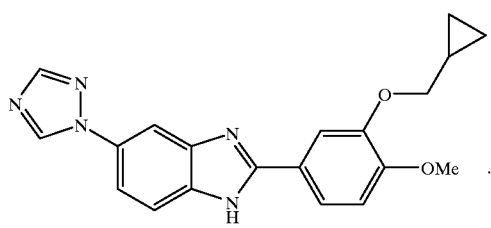

16. The therapeutic agent according to claim 8, wherein said compound is

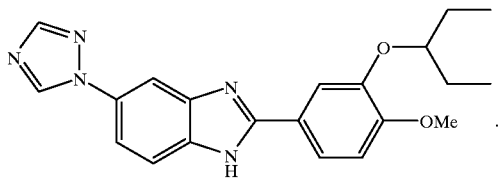

17. The anti-allergic or anti-inflammatory agent according to claim 9, wherein said compound is

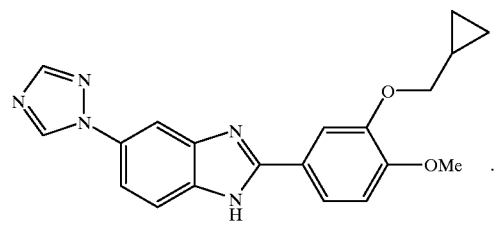

18. The anti-allergic or anti-inflammatory agent according to claim 9, wherein said compound is

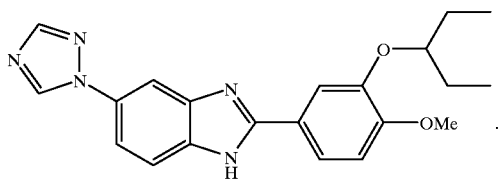

19. The method according to claim 10, wherein A is 1,2,4-triazol-1-yl.

20. The method according to claim 10 or 19, wherein the aliphatic hydrocarbon radical moiety of said aliphatic hydrocarbon radical which may have an alicyclic or aromatic hydrocarbon radical in $R_1$ or $R_2$ is a straight- or branched-chain lower alkyl group having 1 to 6 carbon atoms or a straight- or branched-chain lower alkenyl group having 2 to 6 carbon atoms.

21. The method according to claim 10 or 19, wherein $R_1$ and $R_2$ may be the same or different from each other and each is a methyl, isopropyl, isopentyl, cyclopropylmethyl, cyclopentylmethyl, benzyl, phenylethyl, phenylpropyl, cinnamyl, cyclopentyl, cyclopentenyl, cyclohexyl, cyclohexenyl or cycloheptenyl group.

22. The method according to claim 10 or 19, wherein A is 1,2,4-triazol-1-yl or 1,2,4-triazol-4-yl; $R_1$ and $R_2$ may be the same or different from each other and each is a straight- or branched-chain lower alkyl group having 1 to 6 carbon atoms, which may have a monocyclic alicyclic hydrocarbon radical having 3 to 7 carbon atoms, or a monocyclic alicyclic hydrocarbon radical having 3 to 7 carbon atoms; $R_3$ is a hydrogen atom or a lower alkyl group; and $R_4$ is a hydrogen atom.

23. The method according to claim 22, wherein A is 1,2,4-triazol-1-yl; $R_1$ and $R_2$ may be the same or different from each other and each is a methyl, isopropyl, isopentyl, cyclopropylmethyl, cyclopentylmethyl, cyclopentyl, cyclopentenyl, cyclohexyl, cyclohexenyl or cycloheptenyl group; $R_3$ is a hydrogen atom; and $R_4$ is a hydrogen atom.

24. The method according to claim 10 wherein the benzimidazole derivative compound is
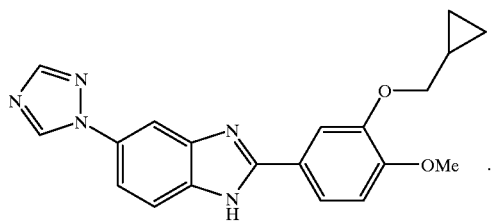
25. The method according to claim 10 wherein the benzimidazole derivative compound is
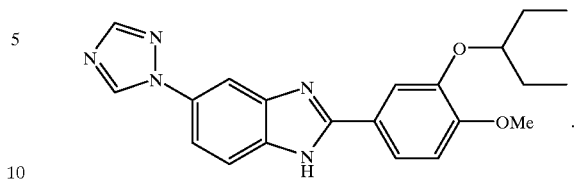
* * * * *